US007766888B2

(12) United States Patent
Mishima et al.

(10) Patent No.: US 7,766,888 B2
(45) Date of Patent: *Aug. 3, 2010

(54) DISPOSABLE DIAPER WITH FECES RETAINING POCKET

(75) Inventors: Yoshitaka Mishima, Kagawa-ken (JP); Kaiyo Nakajima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 522 days.

This patent is subject to a terminal disclaimer.

(21) Appl. No.: 11/101,484

(22) Filed: Apr. 8, 2005

(65) Prior Publication Data

US 2005/0228357 A1    Oct. 13, 2005

(30) Foreign Application Priority Data

Apr. 9, 2004    (JP)    .............................. 2004-115473

(51) Int. Cl.
    *A61F 13/495*    (2006.01)
    *A61F 13/494*    (2006.01)
    *A61F 13/539*    (2006.01)

(52) U.S. Cl. ........................ 604/385.23; 604/385.01; 604/385.19; 604/385.28

(58) Field of Classification Search ............ 604/385.19, 604/385.01, 385.201, 396, 398, 385.24–385.3
    See application file for complete search history.

(56) References Cited

U.S. PATENT DOCUMENTS 3,211,147 A     10/1965   Pherson et al.
3,650,273 A *   3/1972    Schaar ........................... 2/402
3,653,382 A *   4/1972    Easley et al. ................. 604/370
3,776,233 A     12/1973   Schaar
3,816,227 A *   6/1974    Schaar ........................ 428/101
3,848,599 A     11/1974   Schaar
3,885,568 A *   5/1975    Schaar ........................ 604/366
3,943,930 A     3/1976    Schaar
4,573,990 A *   3/1986    Ohsaki ................. 604/385.201
4,695,278 A *   9/1987    Lawson ................. 604/385.27

(Continued)

FOREIGN PATENT DOCUMENTS

EP              955028 A2 *    11/1999

(Continued)

OTHER PUBLICATIONS

Machine Translation of JP 2003-79664.*

(Continued)

*Primary Examiner*—Karin M Reichle
(74) *Attorney, Agent, or Firm*—Lowe Hauptman Ham & Berner, LLP (57) ABSTRACT

In a disposable diaper having a feces retaining pocket formed by body fluid absorbent panel sections overlapping each other in a crotch covering region so that the feces retaining pocket can be largely opened, a second panel section overlaps on a first panel section in the crotch covering region of the diaper to form the feces retaining pocket. The crotch covering region is provided along transversely opposite side edges thereof with elastically stretch- and contractable leak-barrier cuffs. Inner side edges of the respective leak-barrier cuffs are bonded to the second panel section in the vicinity of a rear end of the second panel section lying in the crotch covering region.

22 Claims, 5 Drawing Sheets

U.S. PATENT DOCUMENTS

| | | | |
|---|---|---|---|
| 4,944,735 A | | 7/1990 | Mokry |
| 5,514,121 A | * | 5/1996 | Roe et al. .............. 604/385.19 |
| 5,653,703 A | * | 8/1997 | Roe et al. .............. 604/385.01 |
| 5,954,705 A | * | 9/1999 | Sawaki et al. ......... 604/385.101 |
| 6,869,423 B2 | * | 3/2005 | Onishi et al. ........... 604/385.01 |
| 2002/0007172 A1 | * | 1/2002 | Takei et al. ............. 604/385.27 |
| 2002/0045872 A1 | * | 4/2002 | Shimada et al. .......... 604/385.3 |

FOREIGN PATENT DOCUMENTS

| | | |
|---|---|---|
| EP | 1216678 | 5/2003 |
| EP | 1234563 | 6/2004 |
| FR | 2546745 A1 | 5/1984 |
| GB | 2283663 A | 5/1995 |
| JP | 2002-315778 | 10/2002 |
| JP | 2003-079664 A | 3/2003 |

OTHER PUBLICATIONS

Translation of JP2003-79664/15079664.*
Patent Abstracts of Japan—Publication No. 2002-315778, Published Oct. 29, 2002.
Patent Abstracts of Japan—Publication No. 2003-079664, Published Mar. 18, 2003.
Patent Abstracts of Japan—Publication No. 2002-345871, Published Dec. 3, 2002.
European Patent Office Search Report for EP 05728449 issued Jul. 17, 2007.

* cited by examiner

FIG.5

DISPOSABLE DIAPER WITH FECES RETAINING POCKET

RELATED APPLICATIONS

The present application is based on, and claims priority from, Japanese Application Number 2004-115473, filed Apr. 9, 2004, the disclosure of which is hereby incorporated by reference herein in its entirety.

BACKGROUND OF THE INVENTION

This invention relates to a disposable diaper and to more particularly a disposable diaper formed with a feces retaining pocket.

Japanese Unexamined Patent Application Publication No. 2002-315778 (hereinafter "Reference") discloses a diaper, in which a body fluid absorbent first core is sandwiched between a liquid-pervious sheet and a liquid-impervious sheet to form a relatively large panel extending over a front waist region, a rear waist region and a crotch region. Such a large panel is formed with a feces retaining depression. In this diaper, a relatively small panel comprising a body fluid absorbent second core covered with a liquid-pervious sheet is formed so as to overlap the front waist region and a part of the crotch region on the inner side of the diaper. This relatively small panel covers a part of the feces retaining depression of the relatively large panel in the crotch region so that a pocket opening toward the rear waist region is defined between these relatively large and small panels. Feces flowing from the rear waist region toward the crotch region is reliably received.

The feces retaining pocket of the diaper disclosed in Reference has a size when it is fully opened depending on a vertical dimension from f bottom of the depression to the smaller panel and a transverse dimension of the depression. To ensure that the pocket is adequately opened, the side of the pocket may be dimensioned as largely as desired. However, if a depth of the depression is increased in order to meet this requirement, a thickness of the larger panel will be correspondingly increased and the crotch region of the diaper will become correspondingly bulky. From another viewpoint, if the core of the smaller panel is swollen and/or a stiffness of this core is reduced as the smaller panel absorbs body fluid, the smaller panel may hang into the depression so as to reduce the opening size of the pocket and make it difficult for the pocket to receive feces reliably.

SUMMARY OF THE INVENTION

In view of the problem as has been described above, it is an object of this invention to improve the disposable diaper including the feces retaining pocket formed by overlapping a pair of the panels each other, for example, as disclosed in Reference so that the pocket may be more largely opened.

According to this invention, there is provided a disposable diaper having a back-and-forth direction and a transverse direction being orthogonal to each other, the diaper comprising: a chassis having a front waist covering region, a rear waist covering region and a crotch covering region extending between these two waist covering regions, each of these covering regions having inner side and outer side being opposite to the inner side, the diaper being provided on the inner side, in a middle zone of the crotch covering region as viewed in the transverse direction with a body fluid absorbent panel extending in the back-and-forth direction and further provided along side edges of the diaper being opposite to each other in the transverse direction with leak-barrier cuffs extending in the back-and-forth direction, the leak-barrier cuffs being elastically stretch—and contractable in the back-and-forth direction and partially covering the body fluid absorbent panel.

The diaper further comprises the following structure: The body fluid absorbent panel comprises a first body fluid absorbent panel section having a first rear end lying in the rear waist covering region and a first front end lying in the crotch covering region so as to extend over the rear waist covering region and the crotch covering region, a second body fluid absorbent panel section having a second front end lying in the front waist covering region and a second rear end lying in the crotch covering region so as to extend over the front waist covering region and the crotch covering region wherein the second panel section overlaps the first panel section in the crotch covering region with the second rear end being closer to the wearer's body than the first front end is. The body fluid absorbent panel further comprises, between these first and second panel sections, a third panel section having a third front end being contiguous to the first front end and a third rear end being contiguous to the second rear end;

the first and second panel sections respectively have first and second inner surfaces facing the wearer's body and first and second outer surfaces being opposite to these first and second inner surfaces, the third panel section has a third inner surface facing the first inner surface and a third outer surface being opposite to the first inner surface; of these first, second and third panel sections, at least the first and second panel sections respectively comprise first and second aggregates of body fluid absorbent materials, first and second liquid-pervious inner sheets respectively covering the first and second aggregates so as to define the first and second inner surfaces, and first and second liquid-pervious or liquid-impervious outer sheets covering the first and second aggregates so as to define the first and second outer surfaces; and each of the leak-barrier cuffs comprises a proximal side edge permanently bonded to the respective inner sides of the front waist covering region, the rear waist covering region and the crotch covering region and an elastically stretch—and contractable distal side edge placed aside from the proximal side edge toward a middle zone of the crotch covering region as viewed in the transverse direction wherein the distal side edge is locally bonded with tension in the back-and-forth direction to the second panel section in the vicinity of the second rear end.

In the disposable diaper constructed as has been described above, the second panel section overlaps the first panel section and thereby the feces retaining pocket is formed in the crotch covering region. In the region including this pocket, the leak-barrier cuffs are bonded in a stretched state to the second panel section in a vicinity of the second rear end thereof so that the leak-barrier cuffs contracting as the diaper is put on the wearer and bows in the back-and-forth direction draw up the second rear end of the second panel section off from the first panel. Consequentially, the pocket is largely opened. Even after the second panel section has absorbed body fluid, it is not apprehended that a weight of such body fluid absorbed by the second panel section might reduce the opening area of the pocket because the second panel section is held by the leak-barrier cuffs in its drawn up position.

According to one preferred embodiment, the third panel section comprises a third aggregate of body fluid absorbent material, a third liquid-pervious inner sheets covering the third aggregate so as to define the third inner surface and a third liquid-pervious or liquid-impervious outer sheet covering the third aggregate so as to define the third outer surface.

In the diaper of such an arrangement, the first, second and third panel sections can be easily obtained merely by folding the body fluid absorbent panel extending over the crotch covering region further into the front waist covering region and the rear waist covering region in a generally Z-shape in the crotch covering region.

According to another preferred embodiment, the third panel section comprises a third inner sheet defined by an extension of the first and second inner sheets and a third outer sheet defined by an extension of the first and second outer sheets placed upon each other without interposition of any body fluid absorbent material. In the diaper of such an arrangement, there is no anxiety that the crotch covering region might become bulky because the third panel section is devoid of any body fluid absorbent material.

According to still another preferred embodiment, the second rear end lies aside from a centerline bisecting a dimension of the diaper as measured in the back-and-forth direction toward the front waist covering region. With this diaper, there is no anxiety that loose passage might be mixed with urine and loose passage might contaminate the wearer's skin in a vicinity of the genital organ.

According to further another preferred embodiment, a dimension as measured in the back-and-forth direction over which the first panel section overlaps the second panel section is in a range of 20 to 70 mm. With the diaper dimensioned in this manner, the dimension over which the first panel section overlaps the second panel section may be appropriate to alleviate bulkiness due to these first, second and third panel sections as effectively as possible.

According to an alternative preferred embodiment, the inner side or the outer side in each of the regions is formed from a liquid-impervious sheet. The diaper constructed in this manner is free from an apprehension that the amount of body fluid absorbed by the respective covering regions might leak out of the diaper through the respective covering region.

DETAILED DESCRIPTION OF THE PREFERRED EMBODIMENTS

Details of a disposable diaper according to this invention will be more fully understood from the description given hereunder with reference to the accompanying drawings.

Figure 1:
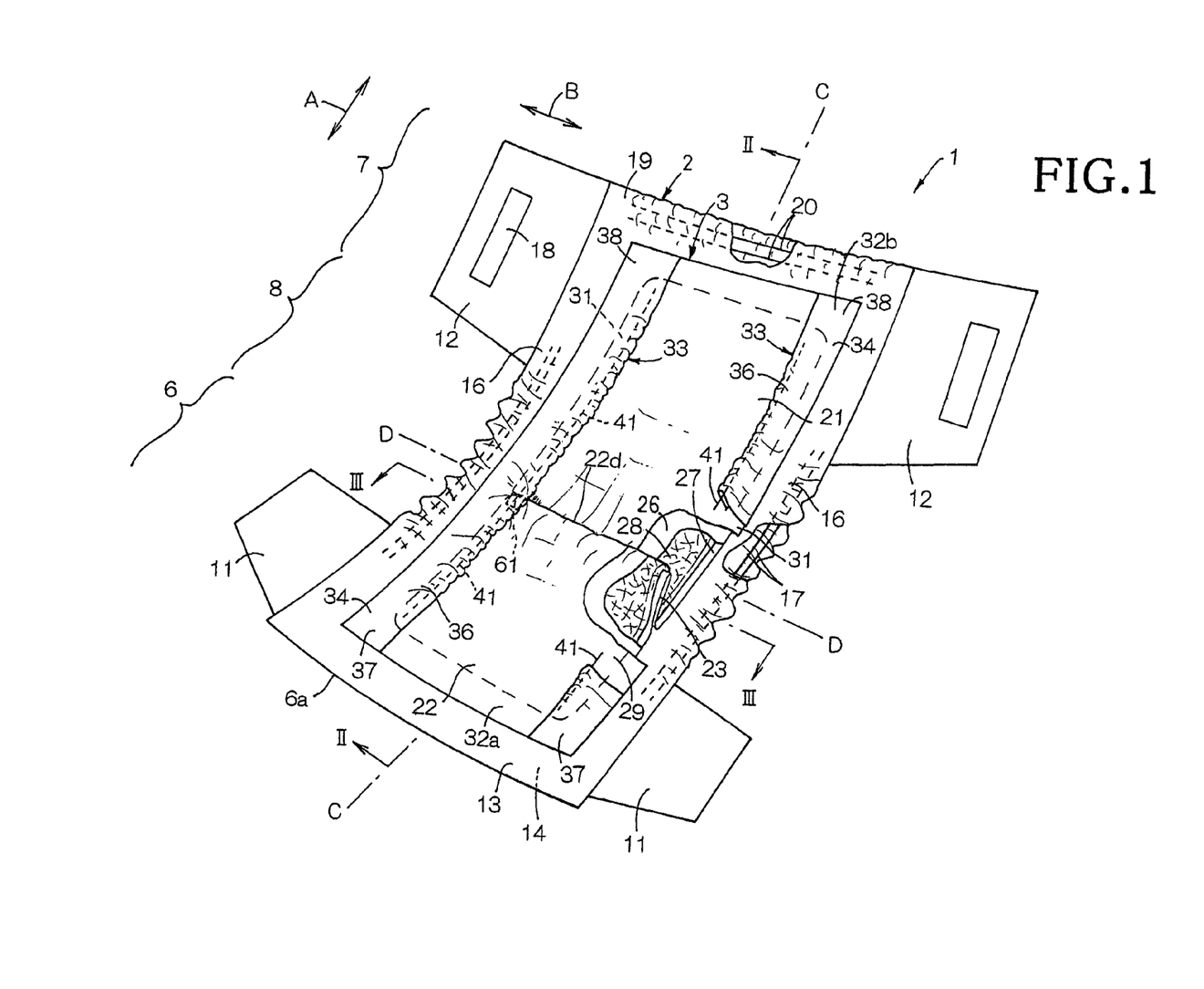
FIG. 1 is a partially cutaway perspective view showing one embodiment of a disposable diaper according to the invention.

A disposable diaper 1 shown in FIG. 1 in a partially cutaway perspective view has a back-and forth direction indicated by a double-headed arrow A and a transverse direction indicated by a double-headed arrow B which is orthogonal to the direction indicated by the double-headed arrow A and comprises a chassis 2 and a body fluid absorbent panel 3. The chassis 2 is shaped in a rectangle which is relatively long in the back-and-forth direction A, defining a front waist covering region 6, a rear waist covering region 7 and a crotch covering region 8 extending between these waist covering regions 6, 7. The front and rear waist covering regions 6, 7 are respectively formed with a pair of front wings 11 and a pair of rear wings 12. The chassis 2 has an inner side 13 facing the wearer's body and an outer side 14 facing the wearer's garment wherein the inner side 13 is defined by a liquid-impervious plastic film and the outer side 14 is defined by a nonwoven fabric laminated on the plastic film. The chassis 2 is provided along transversely opposite side edges 16 extending in the back-and-forth direction A and a rear end 19 extending in the transverse direction B with leg elastic members 17 and a waist elastic member 20, respectively, which are interposed between the plastic film and the nonwoven fabric and secured in a stretched state to at least one of these plastic film and nonwoven fabric. The rear wings 12 are respectively provided on inner surfaces thereof with fasteners 18 such as pressure-sensitives so that the rear wings 12 may be detachably anchored by means of the fasteners 18 on the outer side 14 at desired positions or on outer surfaces of the respective front wings 11 when the diaper 1 is put on the wearer's body.

The absorbent panel 3 laid on the inner side 13 of the chassis 2 comprises a first panel section 21 extending over the rear waist covering region 7 and the crotch covering region 8, a second panel section 22 extending over the front waist covering region 6 and the crotch covering region 8 and a third panel section 23 interposed between these two panel sections 21, 22. The first, second and third panel sections 21, 22, 23 are contiguous one to another in the back-and-forth direction A and formed from inner and outer diffusive sheets 26, 27 both being high in permeability as well as diffusivity for body fluid, a core 28 comprising aggregate of body fluid absorbent materials interposed between these diffusive sheets 26, 27 and a body fluid-pervious topsheet 29 covering the inner diffusive sheet 26. The absorbent panel 3 is contoured by transversely opposite side edges 31 and longitudinally opposite front and rear ends 32a, 32b wherein the side edges 31 are covered with leak-barrier cuffs 33, respectively. Each of the leak-barrier cuffs 33 is formed of elongate nonwoven fabrics, preferably formed of water-repellent or liquid-impervious nonwoven fabrics and having a proximal side edge 34, a distal edge 36 placed aside from the proximal side edge 34 toward a centerline C-C bisecting a width of the diaper 1, a front end 37 and a rear end 38 wherein the proximal side edge 34 and the front and rear ends 37, 38 are bonded to the topsheet 29 or the chassis 2 by means of adhesive or suitable welding technique. An elastic member 41 is secured with tension in the back-and-forth direction A to the distal side edge 36. Referring to FIG. 1, the diaper 1 is shown to curve upward under a contractile force of the leg elastic members 17 and the elastic members 41 attached to the cuffs 33.

Figure 2:
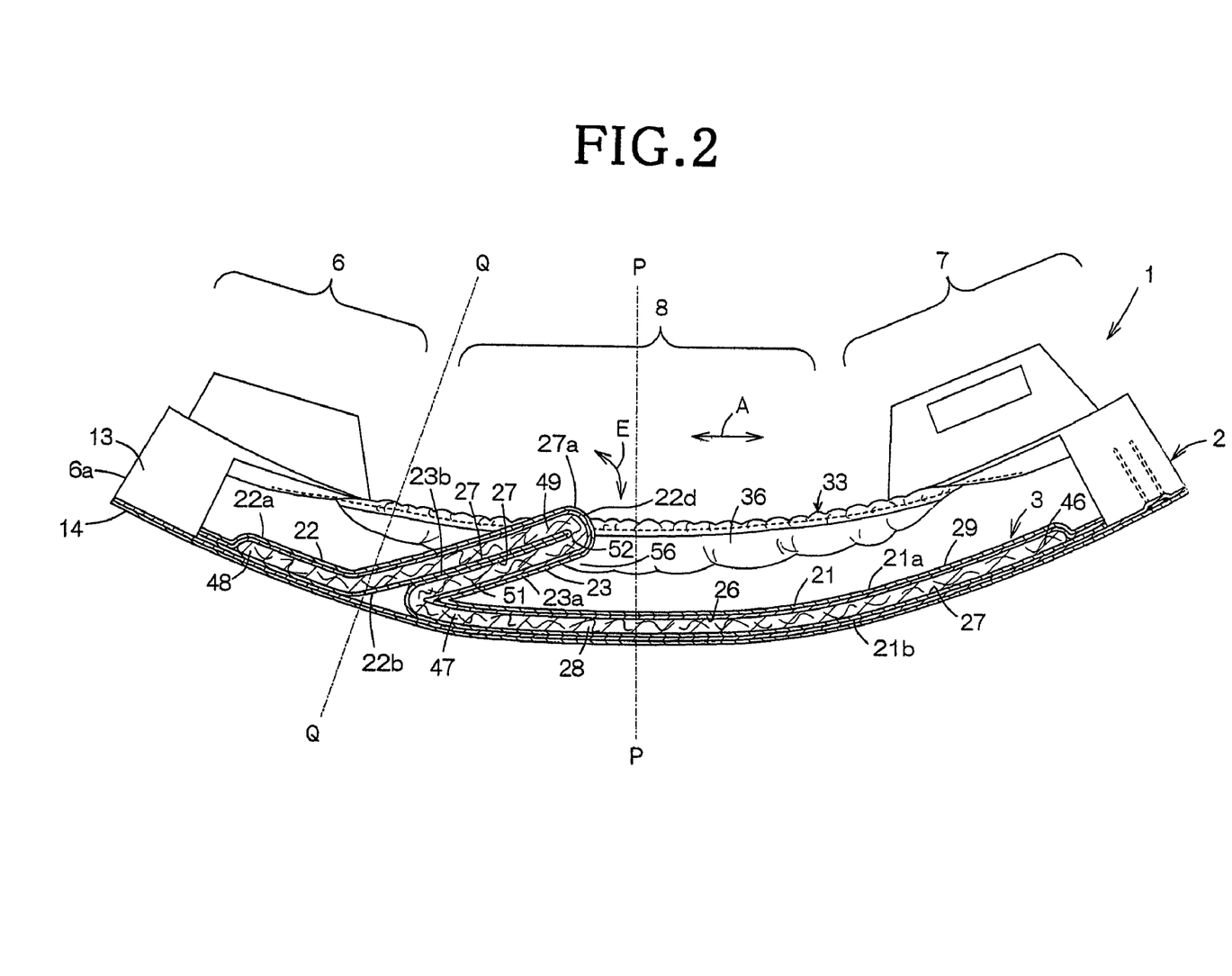
FIG. 2 is a sectional view taken along the line II-II in FIG. 1.

FIG. 2 is a sectional view taken along the line II-II in FIG. 1. The line II-II coincides with the centerline C-C. Of the body fluid absorbent panel 3 laid on the inner side 13 of the chassis 2, the first panel section 21 has a first rear end 46 in the rear waist covering region 7 and a first front end 47 in the crotch covering region 8, the second panel section 22 has a second front end 48 in the front waist covering region 6 and a second rear end 49 in the crotch covering region 8, and the third panel section 23 has a third front end 51 contiguous to the first front end 47 and the third end 52 continuous to the second rear end 49. Preferably, a dimension as measured in the back-and-forth direction over which the first panel section overlaps the second panel section 22 is in a range of 20 to 70 mm. The first panel section 21 has a first inner surface 21a defined by the topsheet 29 and a first outer surface 21b defined by the outer diffusive sheet 27 wherein the first outer surface 21b is bonded to the outer side 13 of the chassis 2 by means of hot melt adhesives (not shown). The second panel section 22 has a second inner surface 22a defined by the topsheet 29 and a second outer surface 22b defined by the outer diffusive sheet 27 wherein the second outer surface 22b is bonded in the vicinity of the second front end 48 to the inner side 13 of the chassis 2 by means of hot melt adhesives (not shown) and, in the vicinity of the second rear end 49 in the crotch covering region 8, lies above the first front end 47 of the first panel section 21. The third panel section 23 interposed between the first panel section 21 and the second panel section 22 in the crotch covering region 8 has a third inner surface 23a and a third outer surface 23b. More specifically, the third inner surface 23a is defined by a segment of the topsheet 29 contiguous to the respective segments of the topsheet 29 in the first panel 21 and the second panel 22 while the third outer surface 23b is defined by a segment of the outer diffusive sheet 27 contiguous to the respective segments of the outer diffusive sheet 27 in the first panel 21 and the second panel 22. The third inner surface 23a is opposed to and movable in and out of contact with the first inner surface 21a of the first panel section 21 while the third outer surface 23b is opposed to the second outer surface 22b of the second panel section 22. In a preferred diaper 1, the segment of the outer diffusive sheet 27 defining the second outer surface 22b of the second panel section 22 is bonded to the segment of the outer diffusive sheet 27 defining the third outer surface 23b of the third panel section 23 by means of hot melt adhesives (not shown). The second rear end 49 of the second panel section 22 and the vicinity thereof left free from the inner side 13 of the chassis 2 can pivot in a direction indicated by a double-headed arrow E to spaced from or to come close to the first inner surface 21a of the first panel section 21 and, when spaced from the first inner surface 21a of the first panel section 21 as shown, a pocket 56 opening toward the rear waist covering region 7 is formed between the first panel 21 and the third panel 23.

Figure 3:
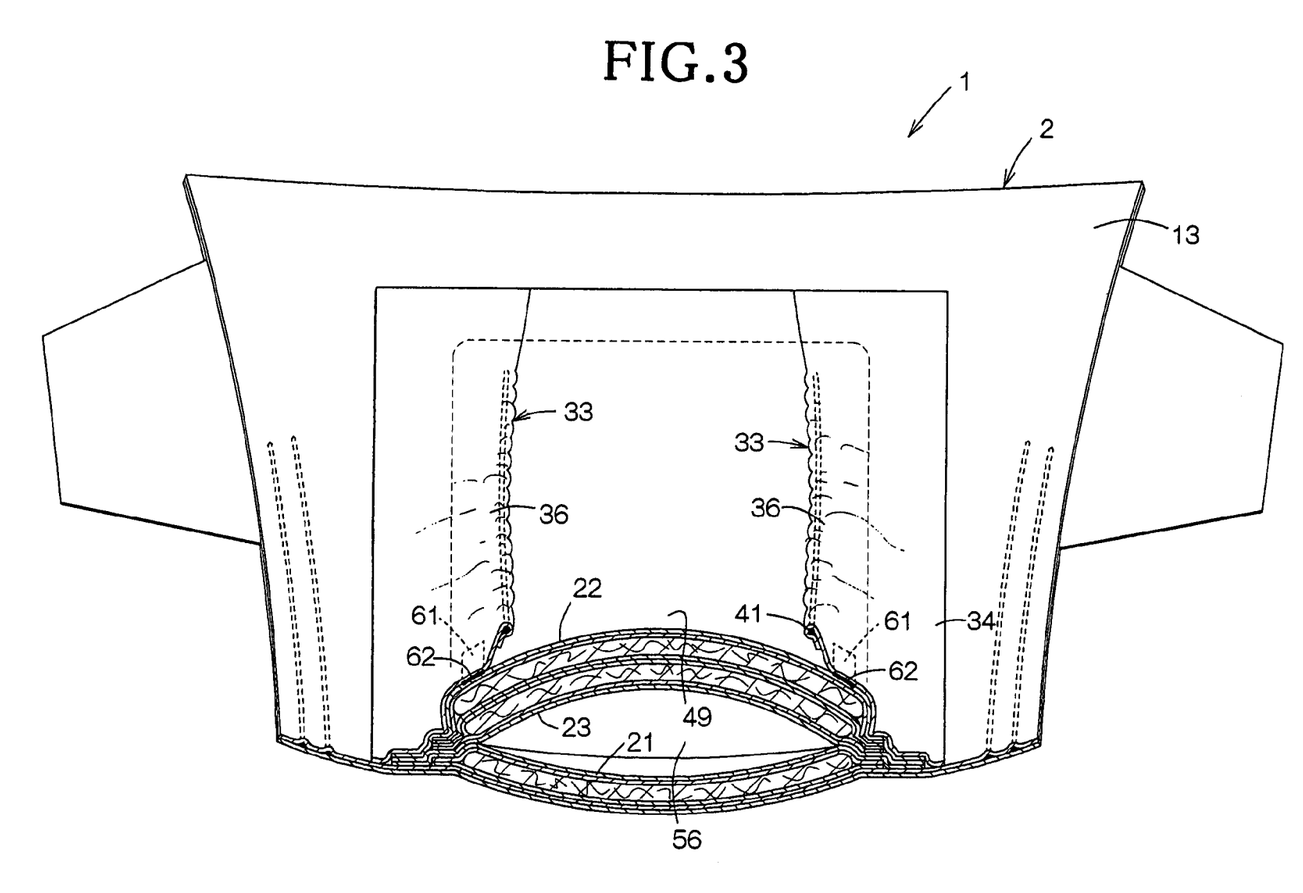
FIG. 3 is a sectional view taken along the line III-III in FIG. 1.

As shown in FIG. 1, in this pocket 56, the second rear end 49 of the second panel section 22 is bonded to the inner side edges 36 of the respective cuffs 33 partially covering the rear end 49 in regions 61 indicated by chain lines using adhesives 62 (See FIG. 3 also). The pocket 56 is obtained by developing and flattening the chassis 2 in the back-and-forth direction A, simultaneously stretching the elastic members 41 in the back-and-forth direction A to collapse the distal side edges 36 of the respective cuffs 33 onto the topsheet 29 of the body fluid absorbent panel 3 and bonding the cuffs 33 in such a state to the second panel 22 in the regions 61. After the cuffs 33 have been bonded to the second panel section 22 in the regions 61, contraction of the elastic members 41 and the leg elastic members 17 causes the diaper 1 to curve as seen in FIGS. 1 and 2. Thereupon, the cuffs 33 move to rise up from the inner side 13 of the chassis 2 with the distal side edges 36 ahead and to draw up the second rear end 49 of the second panel section 22 bonded to the cuffs 33 in the regions 61 together with the third panel section 23 connected to this second end 49 in these regions 61. Such operation of the cuffs 33 causes the pocket 56 to be largely opened. The second panel section 22 cooperates with the third panel section 23 to block a flow of loose passage and urine in the back-and-forth direction A and to guide loose passage into the pocket 56 serving as the feces retaining means. In this way, the second panel section 22 cooperates with the third panel section 23 to prevent loose passage and urine from being mixed with each other. A rear end 22d (See FIGS. 1 and 2) along which these two panel sections 22, 23 are contiguous to each other preferably lies between a line P-P bisecting a dimension of the diaper 1 in the back-and-forth direction A and a line Q-Q bisecting a dimension as measured from the line P-P to a front end 6a of the diaper 1 so that the rear end 22d may be reliably positioned between the wearer's anus and genital organ as the diaper 1 is put on the wearer's body.

FIG. 3 is a sectional view taken along the line III-III in FIG. 1. The leak-barrier cuffs 33 having the respective proximal side edges 34 bonded to the inner side 13 of the chassis 2 along the respective outer side edges 34 have the elastically stretch—and contractable distal side edges 36 bonded in the regions 61 thereof to the second rear end 49 of the second panel section 22 by means of adhesives 62. The pocket 56 is largely opened as the first panel section 21 curve so as to be convex downward while the second panel section 22 and the third panel section 23 are drawn up by the cuffs 33 and bow so as to be convex upward.

The body fluid absorbent panel 3 having such pocket 56 can be obtained by preparing a panel (not shown) having the first, second and third panel sections 21, 22, 23 flatly extending in the back-and-forth direction A and folding, in the crotch covering region 8, this panel in a generally Z-shape as shown by FIG. 2.

Figure 4:
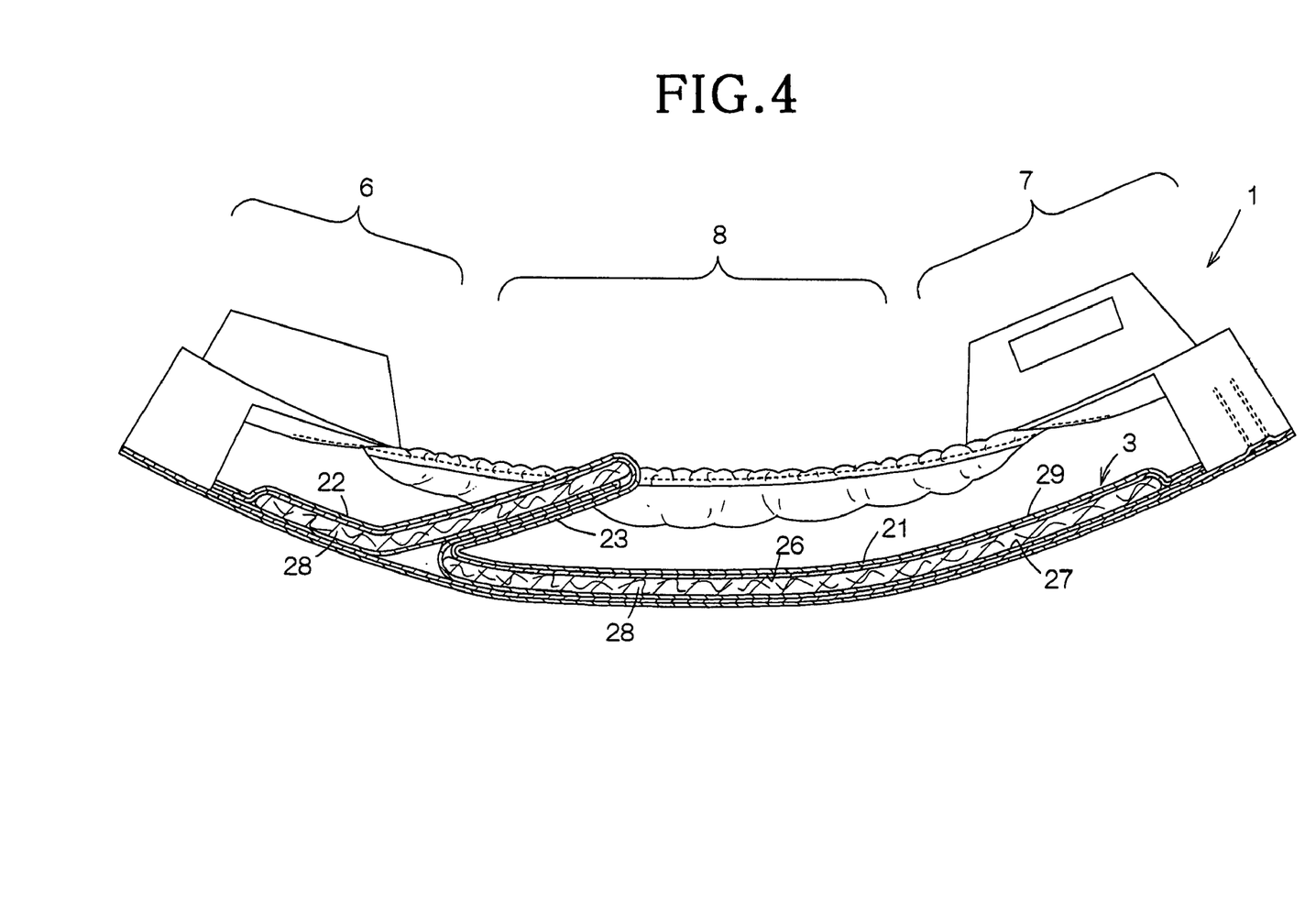
FIG. 4 is a view similar to FIG. 2, showing one preferred embodiment of the invention.

FIG. 4 is a view similar to FIG. 2, showing one preferred embodiment of this invention. While a body fluid absorbent panel 3 in this diaper 1 also comprises first, second and third panel sections 21, 22, 23, the third panel 23 in this diaper 1 is devoid of the core 28 and formed from a topsheet 29, an inner diffusive sheet 26 and an outer diffusive sheet 27 placed one upon another. However, this embodiment is similar to the previous embodiment in that the body fluid absorbent panel 3 can be obtained by folding, in the crotch covering region 8, the panel having the first, second and third panel sections 21, 22, 23 flattened in a generally Z-shape as shown by FIG. 2.

Figure 5:
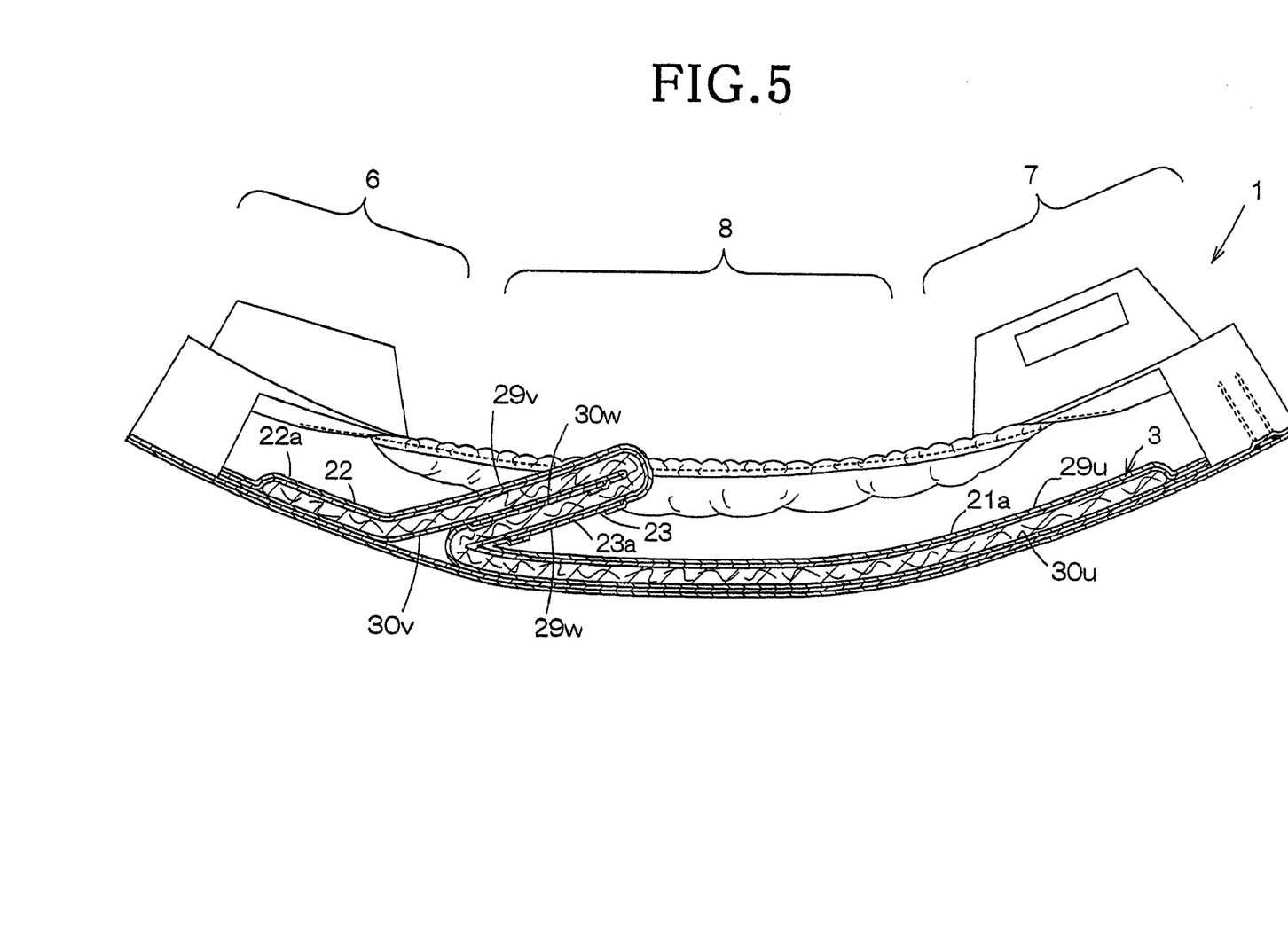
FIG. 5 is a view similar to FIG. 2, showing another preferred embodiment of the invention.

FIG. 5 also is a view similar to FIG. 2, showing another preferred embodiment of this invention. In this diaper 1, a liquid-pervious topsheet 29 defining an inner surface of a body fluid absorbent panel 3 comprises a first topsheet 29u defining a first inner surface 21a of a first panel section 21, a second topsheet 29v defining a second inner surface 22a of a second panel section 22 and a third topsheet 29w defining a third inner surface 23a of a third panel section 23. An outer surface of the absorbent panel 3 comprises, instead of the outer diffusive sheet 27, a first outer sheet 30u defining a first outer surface 21b, a second outer sheet 30v defining a second outer surface 22b and a third outer sheet 30w defining a third outer surface 23b. As materials for the first, second and third topsheets 29u, 29v, 29w, nonwoven fabrics and/or films respectively having different properties may be adopted. For example, nonwoven fabrics having relatively large fiber interstices or plastic films having relatively large apertures may be used as materials for the first topsheet 29u to ensure that the core 28 efficiently traps loose passage and, on the contrary, nonwoven fabrics having relatively small fiber interstices or plastic films having relatively small apertures may be used as materials for the second topsheet 29v to facilitate permeation of urine but to minimize flow back of loose passage from the core 28. While the first, second and third outer sheets 30u, 30v, 30w may be formed using nonwoven fabrics and/or films respectively having different properties, it is also possible to use nonwoven fabrics or films having the same property as the materials for these outer sheets 30u, 30v, 30w. For the diaper 1 according to this embodiment in which the third panel section 23 is devoid of the core 28 as illustrated in FIG. 4, the first and second topsheets 29u, 28v may be liquid-pervious and the third topsheet 29w may be liquid-impervious.

In the diaper 1 according to this invention, the body fluid absorbent core 28 may be formed from an aggregate of body fluid absorbent materials comprising fluff pulp or a mixture of fluff pulp and super-absorbent polymer particles or fibers. The inner diffusive sheet 26 and the outer diffusive sheet 27 sandwiching this core 28 therebetween may be formed from sheet materials which is not only pervious but also diffusive for body fluid such as tissue papers. It should be noted that the inner diffusive sheet 26 is omissible and the outer diffusive sheet 27 may be replaced by a liquid-impervious plastic film. For the diaper 1 in which the absorbent panel 3 having the outer diffusive sheet 27 replaced by a liquid-impervious plastic film, the chassis 2 in FIG. 2 may comprise a nonwoven fabric alone. The chassis 2 in FIG. 2 may be formed also from a nonwoven fabric defining the inner side 13 and a plastic film laminated with this nonwoven fabric so as to define the outer side 14.

This invention makes it possible to make the disposable diaper having the feces retaining pocket adapted to be largely opened.

What is claimed is:

1. A disposable diaper having a back-and-forth direction and a transverse direction orthogonal to each other, said diaper comprising:

a chassis having a front waist covering region, a rear waist covering region and a crotch covering region extending in the back-and-forth direction between said waist covering regions, each of said waist covering regions having an inner side and an outer side opposite to said inner side, a body fluid absorbent panel provided on said inner side, in a middle zone of said crotch covering region as viewed in said transverse direction, said body fluid absorbent panel extending in said back-and-forth direction, and leak-barrier cuffs provided along side edges of said diaper which are opposite to each other in said transverse direction, said leak-barrier cuffs extending in said back-and-forth direction, being elastically stretchable and contractible in said back-and-forth direction, and partially covering said body fluid absorbent panel;

wherein said body fluid absorbent panel comprises a first body fluid absorbent panel section having a first rear end lying in said rear waist covering region and a first front end lying in said crotch covering region so as to extend over said rear waist covering region and said crotch covering region, a second body fluid absorbent panel section having a second front end lying in said front waist covering region and a second rear end lying in said crotch covering region so as to extend over said front waist covering region and said crotch covering region, wherein said second panel section overlaps said first panel section in said crotch covering region with said second rear end being adapted to be closer to a wearer's body than said first front end, while the diaper is worn, and between said first and second panel sections, a third panel section having a third front end being contiguous to said first front end and a third rear end being contiguous to said second rear end;

said first and second panel sections respectively have first and second inner surfaces adapted to face said wearer's body, while the diaper is worn, and first and second outer surfaces opposite to said first and second inner surfaces, respectively;

said third panel section has a third inner surface facing said first inner surface and a third outer surface opposite to said third inner surface, said first and second panel sections respectively comprise first and second aggregates of body fluid absorbent materials, first and second liquid-pervious inner sheets respectively covering said first and second aggregates so as to define said first and second inner surfaces, and first and second liquid-pervious or liquid-impervious outer sheets covering said first and second aggregates so as to define said first and second outer surfaces; and each of said leak-barrier cuffs comprises a proximal side edge bonded to the inner sides of said front waist covering region, said rear waist covering region and said crotch covering region, and an elastically stretchable and contractible distal side edge closer to the middle zone of said crotch covering region than said proximal side edge as viewed in said transverse direction, wherein said distal side edge is locally and directly bonded with tension in said back-and-forth direction to said second panel section in a vicinity of said second rear end; and wherein said second rear end of said second panel section and the vicinity thereof are free from direct attachment to the inner side of said crotch covering region and are pivotable, while the diaper is worn, upward or downward to be spaced from or to come close to said first inner surface of said first panel section following movements of said elastically stretchable and contractible leak-barrier cuffs upward from or downward toward said inner side of said crotch covering region when said cuffs are stretched or contracted, respectively.

2. The diaper as defined by claim 1, wherein said third panel section comprises a third aggregate of body fluid absorbent material, a third liquid-pervious inner sheet covering said third aggregate so as to define said third inner surface, and a third liquid-pervious or liquid-impervious outer sheet covering said third aggregate so as to define said third outer surface.

3. The diaper as defined by claim 1, wherein said third panel section comprises a third inner sheet defined by an extension of said first and second inner sheets, and a third outer sheet defined by an extension of said first and second outer sheets, wherein said third inner sheet and said third outer sheet are placed upon each other without any body fluid absorbent material being disposed therebetween.

4. The diaper as defined by claim 1, wherein said second rear end is closer to said front waist covering region than a centerline bisecting a longitudinal dimension of said diaper as measured in said back-and-forth direction.

5. The diaper as defined by claim 1, wherein a dimension, which is measured in said back-and-forth direction and over which said first panel section overlaps said second panel section, is in a range of 20 to 70 mm.

6. The diaper as defined by claim 1, wherein said inner side or said outer side in each of said regions is formed from a liquid-impervious sheet.

7. The diaper as defined by claim 1, wherein said second outer surface of the second panel section is directly bonded to the third outer surface of the third panel section.

8. A disposable diaper, comprising:

a chassis having a front waist covering region, a rear waist covering region and a crotch covering region extending between said waist covering regions in a longitudinal direction of the diaper, each of said waist and crotch covering regions having an inner side and an outer side being opposite to said inner side, a body fluid absorbent panel extending in said longitudinal direction on the inner side of said crotch covering region and in a middle zone of said crotch covering region as viewed in a transverse direction of said diaper, and leak-barrier cuffs extending in said longitudinal direction along transversely opposite side edges of said chassis, being elastically stretchable and contractible in said longitudinal direction, and partially covering said body fluid absorbent panel;

wherein said body fluid absorbent panel comprises a first body fluid absorbent panel section having a first rear end lying in said rear waist covering region and a first front end lying in said crotch covering region so as to extend over said rear waist covering region and said crotch covering region, a second body fluid absorbent panel section having a second front end lying in said front waist covering region and a second rear end lying in said crotch covering region so as to extend over said front waist covering region and said crotch covering region, wherein said second panel section overlaps said first panel section in said crotch covering region with said second rear end being above said first front end, and between said first and second panel sections, a third panel section having a third front end connected to said first front end and a third rear end connected to said second rear end;

said first and second panel sections respectively have first and second inner surfaces adapted to face a wearer's body, while the diaper is worn, and first and second outer surfaces being opposite to said first and second inner surfaces;

said third panel section has a third inner surface facing said first inner surface and a third outer surface being opposite to said first inner surface;

said first and second panel sections respectively comprise first and second aggregates of absorbent materials, first and second liquid-pervious inner sheets respectively covering said first and second aggregates so as to define said first and second inner surfaces, and first and second outer sheets covering said first and second aggregates so as to define said first and second outer surfaces; and each of said leak-barrier cuffs comprises a proximal side edge bonded to the inner sides of said front waist covering region, said rear waist covering region and said crotch covering region, and an elastically stretchable and contractible distal side edge positioned toward the middle zone of said crotch covering region as viewed in said transverse direction, wherein said distal side edge is bonded to said second panel section in a vicinity of said second rear end thereby biasing the second rear end to rise above the first front end as said distal side edge elastically contracts;

wherein said panel is folded along folding lines where the second and third rear ends meet and where the first and third front ends meet to define said first through third panel sections; and the chassis is not folded along said folding lines.

9. The diaper as defined by claim 8, wherein said third panel section overlaps the first panel section and comprises a third aggregate of absorbent material, a third liquid-pervious inner sheet covering said third aggregate so as to define said third inner surface, and a third liquid-pervious or liquid-impervious outer sheet covering said third aggregate so as to define said third outer surface.

10. The diaper as defined by claim 9, wherein the absorbent materials are distributed to extend continuously from the first panel section to the third panel section and then to the second panel section.

11. The diaper as defined by claim 8, wherein said third panel section overlaps the first panel section, is free of absorbent material, and comprises a third inner sheet defined by an extension of said first and second inner sheets and defining said third inner surface, and a third outer sheet defined by an extension of said first and second outer sheets and defining said third outer surface.

12. The diaper as defined by claim 8, wherein said second rear end lies between a centerline bisecting a dimension of said chassis as measured in said longitudinal direction and said front waist covering region, and is closer to said centerline than to said front waist covering region.

13. The diaper as defined by claim 8, wherein a dimension as measured in said longitudinal direction over which said first panel section overlaps said second panel section is in a range of 20 to 70 mm.

14. The diaper as defined by claim 8, wherein said inner side or said outer side in each of said waist and crotch covering regions is formed from a liquid-impervious sheet.

15. The diaper as defined by claim 8, wherein said second rear end is pivotable towards and away from the chassis and defines, while the diaper is worn, an opening of a pocket between the first and third panel sections.

16. The diaper as defined by claim 15, wherein an upper wall of the pocket is defined by both said second and third panel sections and a lower wall of said pocket is defined by said first panel section; and a thickness of absorbent material in the upper wall is thicker than in the lower wall.

17. The diaper as defined by claim 15, wherein an upper wall of the pocket is defined by both said second and third panel sections and a lower wall of said pocket is defined by said first panel section; and a thickness of absorbent material in the upper wall is about the same as in the lower wall.

18. The diaper as defined by claim 8, wherein the first and second liquid-pervious inner sheets are non-woven fabrics having different fiber interstices or plastic films having different aperture sizes.

19. The diaper as defined by claim 18, wherein said third panel section comprises a third inner sheet being liquid-impervious and defining said third inner surface.

20. The diaper as defined by claim 8, wherein the panel comprises:

an upper diffusive, liquid-pervious sheet that extends continuously from the front waist covering region to the rear waist covering region via the crotch covering region to define the first through third inner surfaces; and a lower diffusive, liquid-pervious sheet that extends continuously from the front waist covering region to the rear waist covering region via the crotch covering region to define the first through third outer surfaces.

21. The diaper as defined by claim 8, wherein the distal side edges of said leak-barrier cuffs are directly bonded to said second panel section in the vicinity of said second rear end and bias, while the diaper is worn, the second rear end to rise above the first front end as said distal side edges elastically contract.

22. The diaper as defined by claim 8, wherein said second outer surface of the second panel section is directly bonded to the third outer surface of the third panel section.

* * * * *